(12) United States Patent  
Handa

(10) Patent No.: US 8,403,821 B2
(45) Date of Patent: Mar. 26, 2013

(54) RADIOTHERAPY APPARATUS CONTROLLER AND RADIATION IRRADIATING METHOD

(75) Inventor: Takanobu Handa, Hiroshima (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 986 days.

(21) Appl. No.: 12/376,555

(22) PCT Filed: Mar. 17, 2008

(86) PCT No.: PCT/JP2008/054878
§ 371 (c)(1),
(2), (4) Date: May 1, 2009

(87) PCT Pub. No.: WO2009/116124
PCT Pub. Date: Sep. 24, 2009

(65) Prior Publication Data
US 2010/0276610 A1    Nov. 4, 2010

(51) Int. Cl.
*A61N 5/00* (2006.01)
(52) U.S. Cl. .............................. 600/1; 378/65
(58) Field of Classification Search .......... 600/1–8; 378/64, 65, 68, 69
See application file for complete search history.

(56) References Cited

U.S. PATENT DOCUMENTS
2007/0211857 A1  9/2007  Urano et al.
2007/0297566 A1  12/2007  Urano et al.

FOREIGN PATENT DOCUMENTS

| JP | 2000-167072 A | 6/2000 |
|---|---|---|
| JP | 2004-136021 A | 5/2004 |
| JP | 2005-518908 A | 6/2005 |
| JP | 3746747 B2 | 12/2005 |
| JP | 2006-21046 A | 1/2006 |
| JP | 2007-236760 A | 9/2007 |
| JP | 2007-282877 A | 11/2007 |
| JP | 2008-456 A | 1/2008 |

*Primary Examiner* — Charles A Marmor, II
*Assistant Examiner* — Carrie R Dorna
(74) *Attorney, Agent, or Firm* — Birch, Stewart, Kolasch & Birch, LLP

(57) ABSTRACT

A radiotherapy apparatus controller includes: an imperfect three-dimensional data calculating unit configured to calculate an imperfect three-dimensional data based on a plurality of imperfect transmission images which is respectively imaged from a plurality of imperfect directions except a predetermined direction among a plurality of directions different from each other; an imaging unit configured to image an additional transmission image from the predetermined direction by using an imager system; a perfect three-dimensional data calculating unit configured to calculate a perfect three-dimensional data based on the additional transmission image and the imperfect three-dimensional data; and a position calculating unit configured to calculate a position of a part of a subject inside based on the perfect three-dimensional data. The radiotherapy apparatus controller can faster calculate the position with higher precision.

22 Claims, 5 Drawing Sheets

RADIOTHERAPY APPARATUS CONTROLLER AND RADIATION IRRADIATING METHOD

TECHNICAL FIELD

The present invention relates to a radiotherapy apparatus controller and a radiation irradiating method, and more particularly relates to a radiotherapy apparatus controller and a radiation irradiating method which are used for curing a patient by irradiating an affected part with radiation.

BACKGROUND ART

Radiotherapy is known which cures a patient by irradiating an affected part (a tumor) with therapeutic radiation. It is desired for the radiotherapy to reduce a dose of the therapeutic radiation radiated to normal cells different from the affected part. As the radiotherapy for curing the affected part (a pulmonary tumor is exemplified) that is moved synchronously with a physiological motion such as a respiration and a heartbeat, a moving body tracking irradiation and a respiration synchronization irradiation (gated irradiation) are applied. The moving body tracking irradiation is a method of changing a radiation direction or radiation field of the therapeutic radiation based on a position of the affected part. The gated irradiation is a method of radiating the therapeutic radiation or stopping the therapeutic radiation based on the position of the affected part. The moving body tracking irradiation and the gated irradiation are preferably such that the dose of the therapeutic radiation radiated to the normal cells different from the affected part is smaller, as compared with an irradiation of an area having a range wider than the area of the affected part. For the moving body tracking irradiation and the gated irradiation, it is desired to measure the position of the affected part more accurately at a higher speed.

Japanese Laid-Open Patent Application (JP-P 2004-136021A) discloses a concentrated irradiation radiotherapy apparatus for creating an image whose artifact caused by scattered rays is little, in parallel to the therapy. The concentrated irradiation radiotherapy apparatus is characterized by including: a first radiation source; a second radiation source; a radiation detector located oppose to the first radiation source with an subject therebetween; a moving mechanism for moving the first and second radiation sources together with the radiation detector to the subject; a first high voltage generator for supplying an electric power to the first radiation source in order to generate radiation for a data collection with a relatively low dose from the first radiation source; a second high voltage generator for supplying an electric power to the second radiation source in order to generate therapeutic radiation with a relatively high dose from the second radiation source; a controller for controlling the second high voltage generator in order to generate the therapeutic radiation from the second radiation source and controlling the first high voltage generator in order to generate the radiation for the data collection from the first radiation source; a compensator for compensating data outputted from the radiation detector correspondingly to a period while the radiation for the data collection is generated from the first radiation source, based on the data outputted from the radiation detector correspondingly to a period while the generation of the radiation for the data collection from the first radiation source is stopped; an image reconfiguring unit for instantly reconfiguring an image data, based on the compensated data; and a display for displaying an mage based on the image data.

Japanese Patent JP3746747B discloses a radiotherapy apparatus that can monitor a state of a therapy field at real time, even during the radiotherapy with radiation. The radiotherapy apparatus includes: a radiation irradiating head for irradiating the therapy field of an subject with the therapeutic radiation; an O-type gantry to which the radiation irradiating head is movably attached; an X-ray source for irradiating the therapy field of the subject with diagnosis X-rays; a sensor array for detecting transmission X-rays of the diagnosis X-rays transmitted through the subject and outputting as a diagnosis image data; an image processor for creating a diagnosis image of the therapy field, based on the diagnosis image data; and a controller. The radiation irradiating head is movably connected to the O-type gantry and includes ahead swinging mechanism for swinging the radiation irradiating head so that the therapy radiation radiated by the radiation irradiating head follows the motion of the therapy field. The controller controls a position of the head swinging mechanism so that the irradiation field of the radiation irradiating head follows the therapy field, based on the diagnosis image, the position of the radiation irradiating head and a swinging state of the radiation irradiating head, and controls irradiation of the radiation irradiating head so that the therapeutic radiation are radiated from the radiation irradiating head, after the positional control of the head swinging mechanism. The sensor array is moved in linkage to the movement of the radiation irradiating head on the O-type gantry.

Japanese Laid-Open Patent Application (JP-P 2006-21046A) discloses a radiotherapy apparatus that can monitor a state of a therapy field at real time, even during the radiotherapy with radiation. The radiotherapy apparatus includes; an O-type gantry; a radiation irradiating head that is movably arranged in the O-type gantry and irradiates the therapy field of an subject with the therapeutic radiation; an X-ray source that is movably arranged in the O-type gantry and irradiates the therapy field of the subject with the diagnosis X-rays; and a sensor array that is movably arranged in the O-type gantry, detects transmission X-rays of the diagnosis X-rays transmitted through the subject, and outputs them as diagnosis image data. The sensor array is arranged at the symmetric position with the radiation irradiating head therebetween and moved in linkage to the movement of the radiation irradiating head on the O-type gantry, and the X-ray source is moved in linkage with the motion of the sensor array.

DISCLOSURE OF INVENTION

An object of the present invention is to provide a radiotherapy apparatus controller and a radiation irradiating method which can detect a predetermined part of a subject with a higher precision at a higher speed.

A radiotherapy apparatus controller according to the present invention includes: an imperfect three-dimensional data calculating unit configured to calculate an imperfect three-dimensional data based on a plurality of imperfect transmission images which is respectively imaged from a plurality of imperfect directions except a predetermined direction among a plurality of directions different from each other; an imaging unit configured to image an additional transmission image from the predetermined direction by using an imager system; a perfect three-dimensional data calculating unit configured to calculate a perfect three-dimensional data based on the additional transmission image and the imperfect three-dimensional data; and a position calculating unit configured to calculate a position of a part of a subject inside based on the perfect three-dimensional data. Typically, the perfect three-dimensional data can be faster calculated based on the additional transmission image and the imperfect three-dimensional data, as compared with the calculation based on a plurality of transmission images respectively imaged from a plurality of directions. Thus, the radiotherapy apparatus controller, after imaging the additional transmission image, can faster calculate the position. Moreover, the radiotherapy apparatus controller can calculate the position with a higher precision, as compared with the calculation of the position in which only the additional transmission image imaged from the predetermined direction is used without using the plurality of imperfect transmission images.

Preferably, the position calculating unit calculates the position of the part of the subject by comparing a reference perfect three-dimensional data, which is calculated based on a plurality of perfect transmission images respectively imaged from the plurality of directions, with the perfect three-dimensional data.

The radiotherapy apparatus controller according to the present invention further includes a shift amount calculating unit configured to calculate a shift amount based on the additional transmission image and the imperfect three-dimensional data. At this time, the perfect three-dimensional data calculating unit calculates the perfect three-dimensional data based on a post-shift transmission image in which an image shown in the additional transmission image is shifted by the shift amount and shown. For example, the radiotherapy apparatus controller can calculate the perfect three-dimensional data which seems to be more presumable, when the shift amount is calculated such that a degree of a blur of the perfect three-dimensional data calculated based on the transmission image is small.

The imperfect three-dimensional data includes a first imperfect three-dimensional data and a second imperfect three-dimensional data different from the first imperfect three-dimensional data. At this time, the perfect three-dimensional data calculating unit prepares a first perfect three-dimensional data based on the additional transmission image and the first imperfect three-dimensional data and calculates a second perfect three-dimensional data based on the additional transmission image and the second imperfect three-dimensional data. The position calculating unit calculates the position based on one of the first imperfect three-dimensional data and the second imperfect three-dimensional data. For example, the radiotherapy apparatus controller can calculate the presumable position, when calculating the position by using the perfect three-dimensional data which is calculated by selecting the imperfect three-dimensional data whose degree of a blur is small, from the first and second imperfect three-dimensional data.

The imperfect three-dimensional data calculating unit calculates another imperfect three-dimensional data based on another plurality of imperfect transmission images which is respectively imaged from another plurality of imperfect directions except another predetermined direction different from the predetermined direction among the plurality of directions. At this time, the imaging unit images another additional transmission image from the other predetermined direction by using the imager system. The perfect three-dimensional data calculating unit calculates another perfect three-dimensional data based on the other additional transmission image and the other imperfect three-dimensional data. The position calculating unit calculates a position of a part of the subject inside based on the other perfect three-dimensional data. Hence, the radiotherapy apparatus controller can calculate the position of the part of the subject inside, even when the imager system is moved to image the transmission image from the other predetermined direction different from the predetermined direction.

The radiotherapy apparatus controller according to the present invention further includes an irradiation controller configured to drive a therapeutic radiation irradiating apparatus radiating the therapeutic radiation based on the position. At this time, the radiotherapy apparatus controller can control the position to which the therapeutic radiation is radiated with a higher precision, as compared with the configuration that the therapeutic radiation irradiating apparatus is driven based on the position calculated based on only the additional transmission image imaged from the predetermined direction.

The therapeutic radiation irradiating apparatus is preferably supported to be moved integrally with the imager system.

A radiotherapy system according to the present invention preferably includes a radiotherapy apparatus controller according to the present invention, a therapeutic radiation irradiating apparatus and an imager system.

A radiation irradiating method according to the present invention includes: calculating an imperfect three-dimensional data based on a plurality of imperfect transmission images which is respectively imaged from a plurality of imperfect directions except a predetermined direction among a plurality of directions different from each other; imaging an additional transmission image from the predetermined direction by using the imager system; calculating a perfect three-dimensional data based on the additional transmission image and the imperfect three-dimensional data; and calculating a position of a part of a subject inside based on the perfect three-dimensional data. Typically, the perfect three-dimensional data can be faster calculated based on the additional transmission image and the imperfect three-dimensional data, as compared with the calculation based on a plurality of transmission images respectively imaged from a plurality of directions. Thus, the radiation irradiating method according to the present invention, after imaging the additional transmission image, can faster calculate the position. Moreover, the radiation irradiating method according to the present invention can calculate the position with the high precision, as compared with the calculation of the position in which only the additional transmission image imaged from the predetermined direction is used without using the plurality of imperfect transmission images.

The position is preferably calculated by comparing a reference perfect three-dimensional data, which is calculated based on a plurality of perfect transmission images respectively imaged from the plurality of directions, with the perfect three-dimensional data.

The radiation irradiating method according to the present invention further includes calculating a shift amount based on the additional transmission image and the imperfect three-dimensional data. At this time, the perfect three-dimensional data is calculated based on a post-shift transmission image in which an image shown in the additional transmission image is shifted by the shift amount and shown. For example, the radiation irradiating method according to the present invention can calculate the perfect three-dimensional data which seems to be presumable, when the shift amount is calculated such that a degree of a blur of the perfect three-dimensional data calculated based on the transmission image is small.

The imperfect three-dimensional data includes a first imperfect three-dimensional data and a second imperfect three-dimensional data different from the first imperfect three-dimensional data. At this time, the position is calculated based on one of the first perfect three-dimensional data prepared based on the additional transmission image and the first imperfect three-dimensional data and the second perfect three-dimensional data prepared based on the additional transmission image and the second imperfect three-dimensional data. For example, the radiation irradiating method according to the present invention can calculate the presumable position, when calculating the position by using the perfect three-dimensional data which is calculated by selecting the imperfect three-dimensional data whose degree of a blur is small, from the first and second imperfect three-dimensional data.

The radiation irradiating method according to the present invention further includes: calculating another imperfect three-dimensional data based on another plurality of imperfect transmission images which is respectively imaged from another plurality of imperfect directions except another predetermined direction different from the predetermined direction among the plurality of directions; imaging another additional transmission image from the other predetermined direction by using the imager system; calculating another perfect three-dimensional data based on the other additional transmission image and the other imperfect three-dimensional data; and calculating a position of a part of the subject inside based on the other perfect three-dimensional data. At this time, the radiation irradiating method according to the present invention can calculate the position of the part of the subject inside, even when the imager system is moved to image the transmission image from the other predetermined direction different from the predetermined direction.

The radiation irradiating method according to the present invention further includes driving a therapeutic radiation irradiating apparatus radiating the therapeutic radiation based on the position. At this time, the radiation irradiating method according to the present invention can control the position to which the therapeutic radiation is radiated with a high precision, as compared with the configuration that the therapeutic radiation irradiating apparatus is driven based on the position calculated based on only the additional transmission image imaged from the predetermined direction.

BEST MODE FOR CARRYING OUT THE INVENTION

Figure 1:
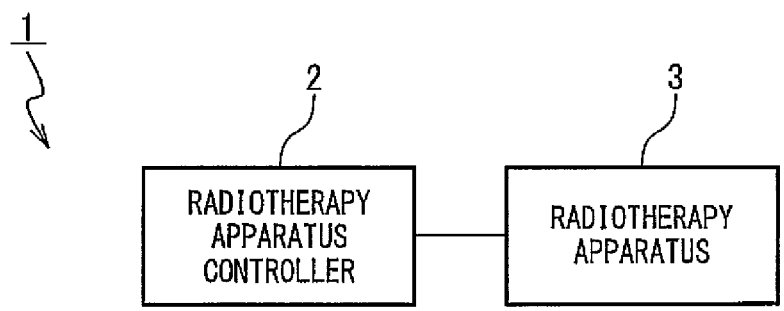
FIG. 1 is a block diagram showing an embodiment of a radiotherapy system according to the present invention.

An embodiment of a radiotherapy apparatus controller according to the present invention will be described below with reference to the drawings. The radiotherapy apparatus controller 2 is applied to a radiotherapy system 1, as shown in FIG. 1. The radiotherapy system 1 includes the radiotherapy apparatus controller 2 and a radiotherapy apparatus 3. The radiotherapy apparatus controller 2 is a computer exemplified by a personal computer. The radiotherapy apparatus controller 2 is connected to the radiotherapy apparatus 3 so that information can be bi-directionally transmitted.

Figure 2:
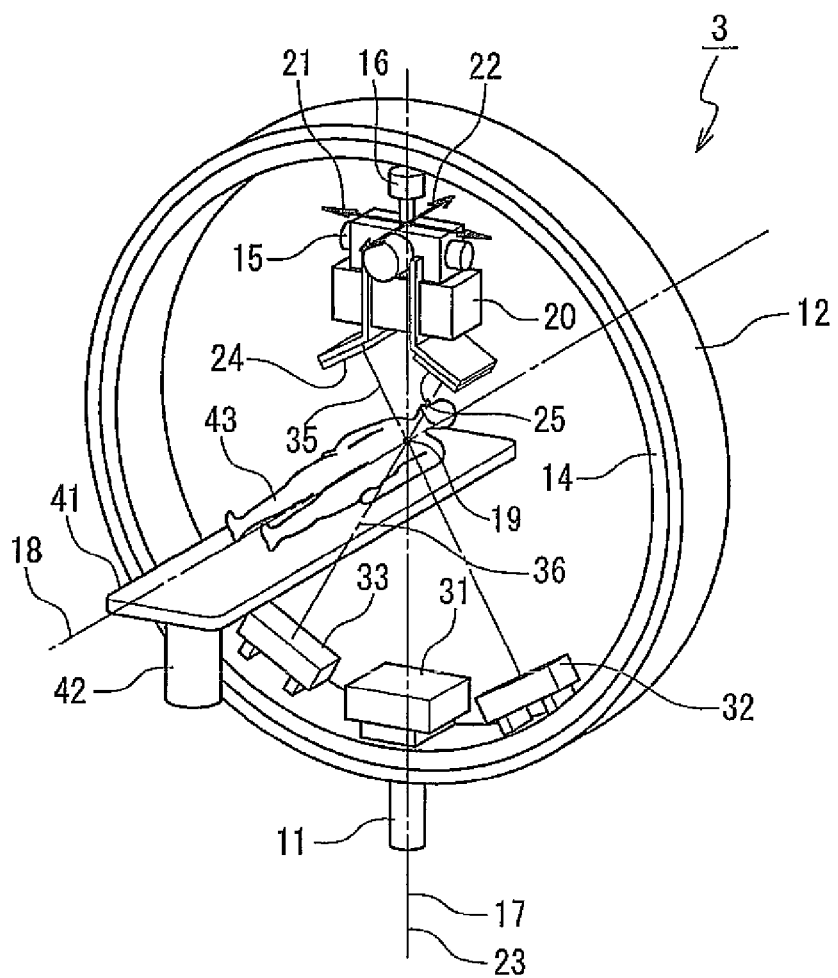
FIG. 2 is a perspective view showing a radiotherapy apparatus.

FIG. 2 shows the radiotherapy apparatus 3. The radiotherapy apparatus 3 includes a pivoting driver 11, an O-ring 12, a traveling gantry 14, a head swinging mechanism 15 and a therapeutic radiation irradiating apparatus 16. The pivoting driver 11 supports the O-ring 12 on a base so that the O-ring 12 can be rotated around a rotational axis 17. The pivoting driver 11 is controlled by the radiotherapy apparatus controller 2 and rotates the O-ring 12 around the rotational axis 17. The rotational axis 17 is parallel to a perpendicular direction. The O-ring 12 is ring-shaped around a rotational axis 18 and supports the traveling gantry 14 rotatably around the rotational axis 18. The rotational axis 18 is vertical to the perpendicular direction and passes through an isocenter 19 included in the rotational axis 17. The rotational axis 18 is further fixed with respect to the O-ring 12, namely, rotated together with the O-ring 12 around the rotational axis 17. The traveling gantry 14 is ring-shaped around the rotational axis 18, and arranged concentrically with a ring of the O-ring 12. The radiotherapy apparatus 3 further includes a traveling driver which is not shown. The traveling driver is controlled by the radiotherapy apparatus controller 2 and rotates the traveling gantry 14 around the rotational axis 18.

The head swinging mechanism 15 is fixed inside the ring of the traveling gantry 14 and supports the therapeutic radiation irradiating apparatus 16 to the traveling gantry 14 so that the therapeutic radiation irradiating apparatus 16 is arranged inside the traveling gantry 14. The head swinging mechanism 15 has a pan axis 21 and a tilt axis 22. The tilt axis 22 is fixed with respect to the traveling gantry 14 and parallel to the rotational axis 18 without intersecting the rotational axis 18. The pan axis 21 is orthogonal to the tilt axis 22. The head swinging mechanism 15 is controlled by the radiotherapy apparatus controller and rotates the therapeutic radiation irradiating apparatus 16 around the pan axis 21 and rotates the therapeutic radiation irradiating apparatus 16 around the tilt axis 22.

The therapeutic radiation irradiating apparatus 16 is controlled by the radiotherapy apparatus controller 2 and radiates therapeutic radiation 23. The therapeutic radiation 23 is radiated substantially along a straight line passing through the intersection at which the pan axis 21 and the tilt axis 22 intersect. The therapeutic radiation 23 is generated to have a uniform magnitude distribution. The therapeutic radiation irradiating apparatus 16 has an MLC (Multi Leaf Collimator) 20. The MLC 20 is controlled by the radiotherapy apparatus controller 2 and shields a part of the therapeutic radiation 23 and consequently changes a shape of the irradiation field when a patient is irradiated with the therapeutic radiation 23.

Once the therapeutic radiation irradiating apparatus 16 is adjusted to face the isocenter 19 by the head swinging mechanism 15 because the therapeutic radiation irradiating apparatus 16 is supported by the traveling gantry 14 as mentioned above, the therapeutic radiation 23 always substantially passes through the isocenter 19, even when the O-ring 12 is rotated by the pivoting driver 11 or when the traveling gantry 14 is rotated by the traveling driver. That is, since the traveling and the pivoting are carried out, the therapeutic radiation 23 can be radiated from any direction to the isocenter 19.

The radiotherapy apparatus 3 further includes a plurality of imager systems. That is, the radiotherapy apparatus 3 includes diagnosis X-ray sources 24, 25 and sensor arrays 32, 33. The diagnosis X-ray source 24 is supported by the traveling gantry 14. The diagnosis X-ray source 24 is arranged inside the ring of the traveling gantry 14 and arranged at a position at which an angle between a line from the isocenter 19 to the diagnosis X-ray source 24 and a line from the isocenter 19 to the therapeutic radiation irradiating apparatus

16 is acute. The diagnosis X-ray source 24 is controlled by the radiotherapy apparatus controller 2 and radiates diagnosis X-ray 35 to the isocenter 19. The diagnosis X-ray 35 is radiated from one point of the diagnosis X-ray source 24 and exhibit a conical cone beam in which the foregoing one point serves as an apex. The diagnosis X-ray source 25 is supported by the traveling gantry 14. The diagnosis X-ray source 25 is arranged inside the ring of the traveling gantry 14 and arranged at a position at which an angle between a line from the isocenter 19 to the diagnosis X-ray source 25 and the line from the isocenter 19 to the therapeutic radiation irradiating apparatus 16 is acute. The diagnosis X-ray source 25 is controlled by the radiotherapy apparatus controller 2 and radiates diagnosis X-ray 36 to the isocenter 19. The diagnosis X-ray 36 is radiated from one point of the diagnosis X-ray source 25 and exhibit a conical cone beam in which the foregoing one point serves as an apex.

The sensor array 32 is supported by the traveling gantry 14. The sensor array 32 receives the diagnosis X-ray 35, which is radiated by the diagnosis X-ray source 24 and transmitted through a subject around the isocenter 19, and creates a transmission image of the subject. The sensor array 33 is supported by the traveling gantry 14. The sensor array 33 receives the diagnosis X-ray 36, which is radiated by the diagnosis X-ray source 25 and transmitted through the subject around the isocenter 19, and creates a transmission image of the subject. As the sensor arrays 32, 33, FPD (Flat Panel Detector) and an X-ray II (Image Intensifier) are exemplified.

According to the imager systems, the transmission images whose center are the isocenter 19 can be created based on image signals obtained from the sensor arrays 32, 33.

The radiotherapy apparatus 3 further includes a sensor array 31. The sensor array 31 is arranged such that a line between the sensor array 31 and the therapeutic radiation irradiating apparatus 16 passes through the isocenter 19. The sensor array 31 is fixed inside the ring of the traveling gantry 14. The sensor array 31 receives the therapeutic radiation 23, which is radiated by the therapeutic radiation irradiating apparatus 16 and transmitted through the subject around the isocenter 19, and creates a transmission image of the subject. As the sensor array 31, the FPD and the X-ray II are exemplified.

The radiotherapy apparatus 3 further includes a couch 41 and a couch driver 42. The couch 41 is used as a place where a patient 43, who is cured by the radiotherapy system 1, lies thereon. The couch 41 includes a fixing tool which is not shown. The patient is fixed onto the couch 41 by the fixing tool so that the patient does not move. The couch driver 42 supports the couch 41 on the base, and this is controlled by the radiotherapy apparatus controller 2 and moves the couch 41.

Figure 3:
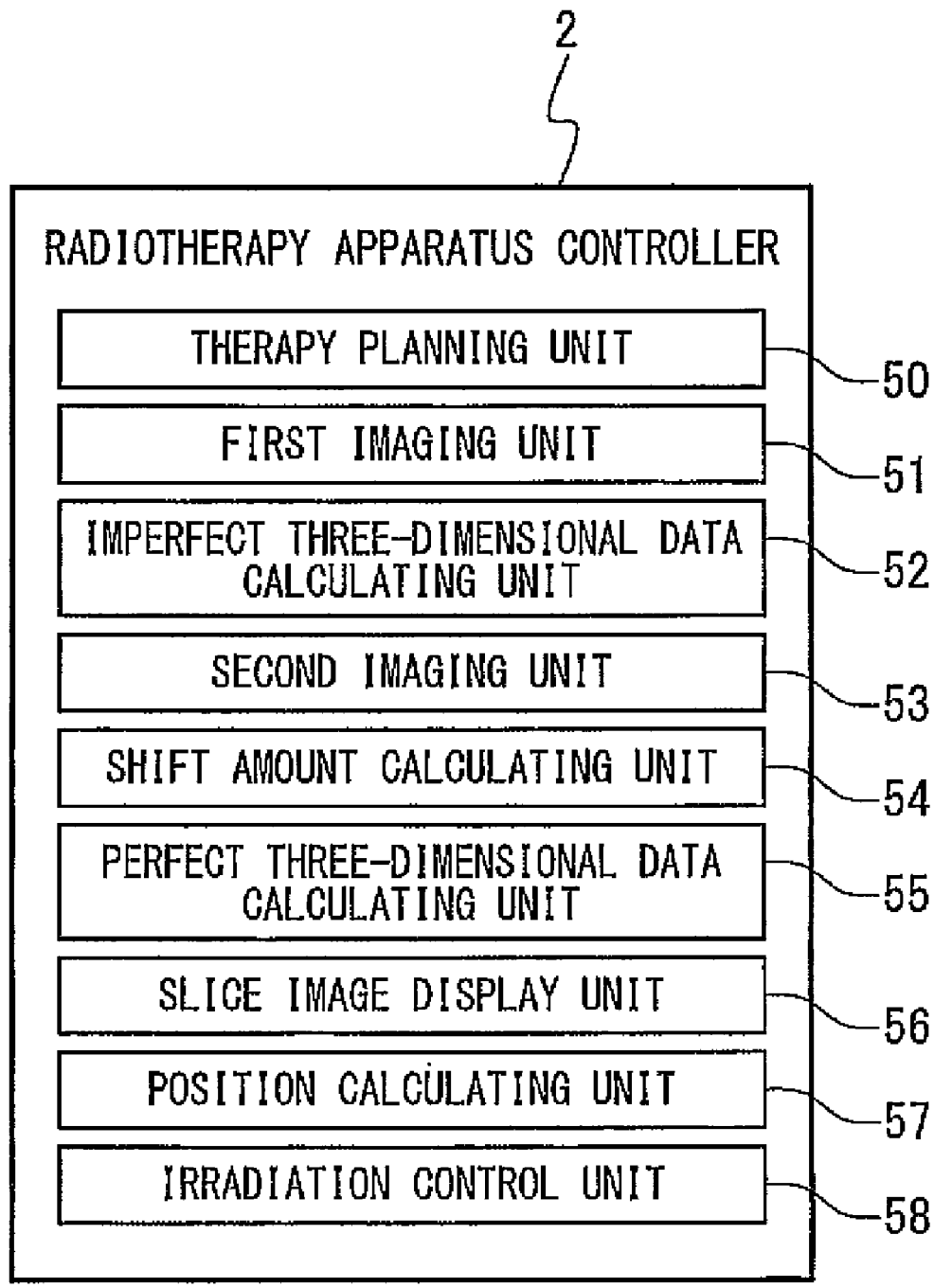
FIG. 3 is a block diagram showing a radiotherapy apparatus controller.

FIG. 3 shows the radiotherapy apparatus controller 2. The radiotherapy apparatus controller 2 is a computer and includes a CPU, a storing unit, an input unit, an output unit and an interface, which are not shown. The CPU executes a computer program, which is installed in the radiotherapy apparatus controller 2, and controls the storing unit, the input unit and the output unit. The storing unit records the computer program, records information used in the CPU and records information prepared by the CPU. The input unit outputs information, which is prepared by an operation of a user, to the CPU. As the input unit, a keyboard and a mouse are exemplified. The output unit recognizably outputs information prepared by the CPU to the user. As the output unit, a display is exemplified. The interface outputs information, which is prepared by external devices connected to the radiotherapy apparatus controller 2, to the CPU, and outputs information prepared by the CPU to the external devices. The external devices include the pivoting driver 11, the traveling driver, the head swinging mechanism 15, the therapeutic radiation irradiating apparatus 16, the MLC 20, the imager system (the diagnosis X-ray sources 24, 25 and the sensor arrays 31, 32 and 33) and the couch driver 42, in the radiotherapy apparatus 3.

The computer program includes a therapy planning unit 50, a first imaging unit 51, an imperfect three-dimensional data calculating unit 52, a second imaging unit 53, a shift amount calculating unit 54, a perfect three-dimensional data calculating unit 55, a slice image display unit 56, a position calculating unit 57 and an irradiation control unit 58.

The therapy planning unit 50 displays the three-dimensional data of the patient 43, which is prepared by a computed tomography apparatus (not shown), on the output unit so that the three-dimensional data can be viewed by the user. The therapy planning unit 50 further prepares a therapy plan based on information inputted by using the input unit. The therapy plan indicates the three-dimensional data of the patient 43 and indicates a combination of irradiation angles and doses. The irradiation angle indicates a direction in which the therapeutic radiation 23 are radiated to an affected part of the patient 43 and indicates an O-ring rotation angle and a gantry rotation angle. The O-ring rotation angle indicates a position of the O-ring 12 with respect to the base. The gantry rotation angle indicates a position of the traveling gantry 14 with respect to the O-ring 12. The dose indicates a dose of the therapeutic radiation 23 radiated to the patient 43 from each irradiation angle.

The first imaging unit 51 rotates the O-ring 12 around the rotational axis 17 by using the pivoting driver 11 and then places the O-ring 12 at the O-ring rotation angle that is indicated by the therapy plan prepared by the therapy planning unit 50. The first imaging unit 51 rotates the traveling gantry 14 by 200 degrees around the rotational axis 18 by using the traveling driver in the radiotherapy apparatus 3. At this time, the first imaging unit 51 images a transmission image of the patient 43 by using the imager system in the radiotherapy apparatus 3, each time the traveling gantry 14 is rotated by 0.5 degrees. That is, the first imaging unit 51 images the 400 transmission images by using the diagnosis X-rays 35, 36 which are radiated to the patient 43 from 400 directions different from each other.

The first imaging unit 51 further correlates the plurality of transmission images to the angle information and temporarily records in the storing unit. That is, any element in the plurality of transmission images corresponds to one element of the angle information. The angle information indicates the directions in which the diagnosis X-rays 35 or 36 are radiated to the patient 43, when the transmission images are imaged.

The imperfect three-dimensional data calculating unit 52 calculates a imperfect three-dimensional data by reconfiguring the transmission images except some of transmission images among the plurality of transmission images imaged by the first imaging unit 51. The some of transmission images indicates the transmission images imaged by the imager system in the radiotherapy apparatus 3, when the therapeutic radiation irradiating apparatus 16 is arranged such that the therapeutic radiation 23 is radiated from the irradiation angle indicated by the therapy plan which is prepared by the therapy planning unit 50.

The second imaging unit 53 images a transmission image of the patient 43 by using the imager system in the radiotherapy apparatus 3, when the therapeutic radiation irradiating apparatus 16 is arranged such that the the image is shown in the transmission image imaged by the second imaging unit 53. That is, the shift amount calculating unit 54 calculates the shift amount base on the transmission image imaged by the second imaging unit 53 and the imperfect three-dimensional data calculated by the imperfect three-dimensional data calculating unit 52.

The perfect three-dimensional data calculating unit 55 calculates the reference perfect three-dimensional data by reconfiguring the plurality of transmission images imaged by the first imaging unit 51. The reference perfect three-dimensional data indicates the patient 43 in three dimensions, when the plurality of transmission images is imaged by the first imaging unit 51.

The perfect three-dimensional data calculating unit 55 further calculates the post-shift transmission image based on the transmission image imaged by the second imaging unit 53 and the shift amount calculated by the shift amount calculating unit 54. The post-shift transmission image indicates the transmission image in which the image shown in the transmission image imaged by the second imaging unit 53 is shifted by the shift amount calculated by the shift amount calculating unit 54 and shown.

The perfect three-dimensional data calculating unit 55 calculates the perfect three-dimensional data based on the post-shift transmission image and the imperfect three-dimensional data calculated by the imperfect three-dimensional data calculating unit 52. The perfect three-dimensional data indicates the patient 43 in the three dimensions, when the plurality of transmission images is imaged by the second imaging unit 53.

The slice image display unit 56 displays a state inside the patient 43 on the display based on the perfect three-dimensional data calculated by the perfect three-dimensional data calculating unit 55 so that the state can be recognized by the user. For example, the slice image display unit 56 calculates a slice image based on the perfect three-dimensional data calculated by the perfect three-dimensional data calculating unit 55. The slice image indicates a sectional image of the patient 43 at a time when the transmission image is imaged by the second imaging unit 53. The slice image display unit 56 further displays the slice image on the display.

The position calculating unit 57 calculates a position of the affected part of the patient 43, by comparing the reference perfect three-dimensional data calculated by the perfect three-dimensional data calculating unit 55 and the perfect three-dimensional data. Incidentally, the position calculating unit 57 can also calculate the position of the affected part of the patient 43 by using another calculating method that does not use the reference perfect three-dimensional data. As the calculating method, a method is exemplified which measures in advance the relation between a position of the affected part and a blur amount indicating a blur degree of the image of the affected part therapeutic radiation 23 is radiated at the irradiation angle indicated by the therapy plan which is prepared by the therapy planning unit 50. The transmission image shows the patient 43.

The shift amount calculating unit 54 calculates a plurality of post-shift transmission images, in each of which an image shown in the transmission image imaged by the second imaging unit 53 is slightly shifted and shown. The shift amount calculating unit 54 calculates a plurality of perfect three-dimensional data, for each of the plurality of calculated post-shift transmission images, based on each of the calculated post-shift transmission images and the imperfect three-dimensional data calculated by the imperfect three-dimensional data calculating unit 52. The shift amount calculating unit 54 selects the perfect three-dimensional data having the smallest difference from a reference perfect three-dimensional data which is calculated based on only the plurality of transmission images imaged by the first imaging unit 53, from the plurality of calculated perfect three-dimensional data. The shift amount calculating unit 54 calculates a shift amount based on the post-shift transmission image used to calculate the selected perfect three-dimensional data and the transmission image imaged by the second imaging unit 53. The shift amount indicates a direction and distance deviated from a position where a certain image is shown in the post-shift transmission image to a position where that is shown in the perfect three-dimensional data, and refers to the relation and then calculates the position of the affected part based on the blur amount of the image of the affected part shown in the calculated perfect three-dimensional data.

The irradiation control unit 58 drives the therapeutic radiation irradiating apparatus 16 by using the head swinging mechanism 15 so that the therapeutic radiation 23 is transmitted through the position of the affected part calculated by the position calculating unit 57, and controls the shape of the irradiation field of the therapeutic radiation 23 by using the MLC 20. The irradiation control unit 58, after driving the head swinging mechanism 15 and the MLC 20, radiates the therapeutic radiation 23 by using the therapeutic radiation irradiating apparatus 16. Incidentally, the irradiation control unit 58 can also change a positional relation between the patient 43 and the therapeutic radiation irradiating apparatus 16, by further using the pivoting driver 11, the traveling driver or the couch driver 42, so that the therapeutic radiation 23 is transmitted through the affected part.

Figure 4:
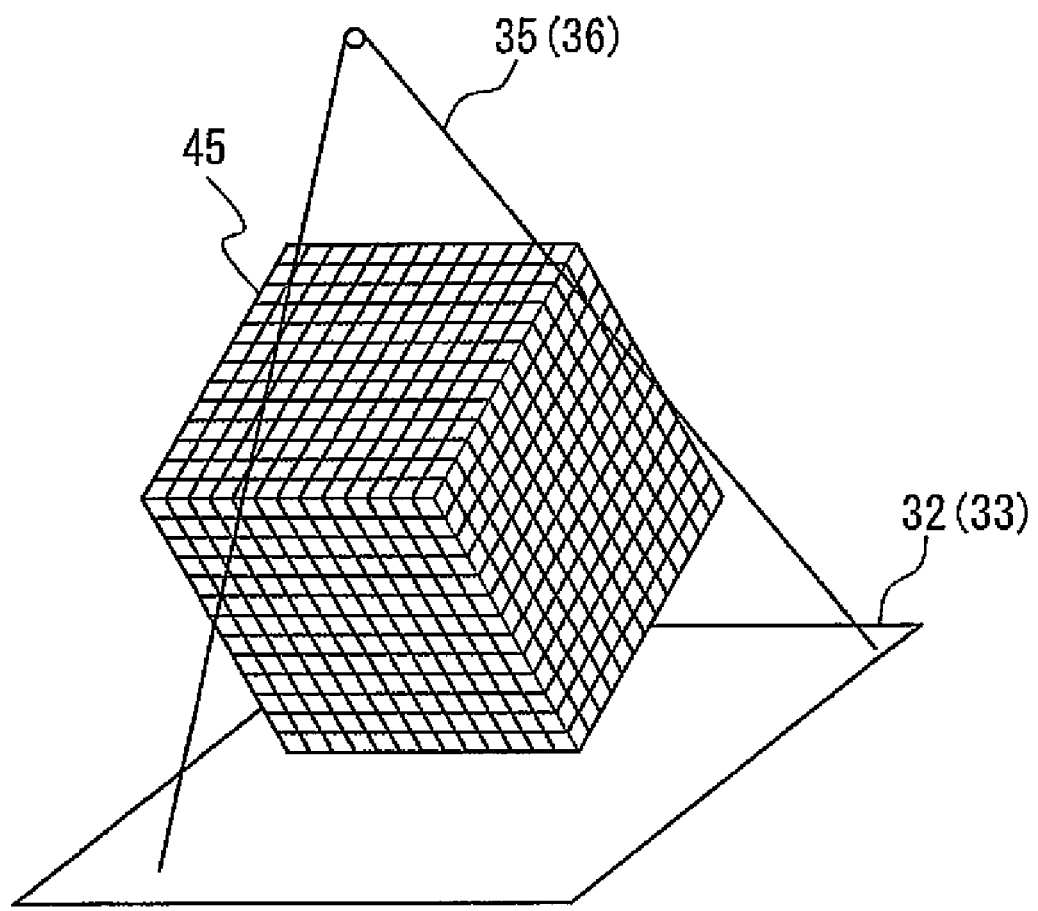
FIG. 4 is a conceptual view showing a three-dimensional data.

FIG. 4 shows the perfect three-dimensional data calculated by the perfect three-dimensional data calculating unit 55. In the perfect three-dimensional data 45, a plurality of transmission factors is correlated to a plurality of voxels. The plurality of voxels respectively corresponds to a plurality of cubes which is filled in space where the patient 43 is placed, without any gap. As a length of one side of the cube, 0.4 mm is exemplified. The transmission factor corresponding to each voxel indicates a transmission factor of the X-ray of the cube at a position corresponding to each voxel. At this time, the position of the affected part of the patient 43 that is calculated based on the perfect three-dimensional data 45 is higher in precision than the position of the affected part of the patient 43 that is calculated based on only the two transmission images.

The perfect three-dimensional data 45 is calculated based on the plurality of transmission images that is respectively imaged based on the diagnosis X-rays 35 (36) radiated to the patient 43 from the plurality of directions different from each other, or calculated based on the imperfect three-dimensional data and the two transmission images. The imperfect three-dimensional data is calculated based on the plurality of transmission images that is respectively imaged based on the diagnosis X-rays 35 (36) radiated to the patient 43 from the plurality of directions except the direction of the diagnosis X-rays 35 (36) used to image the two transmission images. In the perfect three-dimensional data 45, the calculation amount calculated based on the imperfect three-dimensional data is smaller than the calculation amount calculated based on only the plurality of transmission images. Thus, the perfect three-dimensional data 45 can be faster calculated based on the imperfect three-dimensional data, as compared with the calculation based on only the plurality of transmission images.

An embodiment of the radiation irradiating method according to the present invention is executed by using the radiotherapy system 1 and includes an operation of preparing the therapy plan, the operation of preparing the imperfect three-dimensional data, and the operation of carrying out the radiotherapy.

In the operation of preparing the therapy plan, at first, an user inputs a three-dimensional data of the patient 43, which is prepared by a computed tomography apparatus, to the radiotherapy apparatus controller 2. The radiotherapy apparatus controller 2 creates an image indicating an affected part of the patient and organs around the affected part based on the three-dimensional data. The user views the image and specifies a position of the affected part by using the radiotherapy apparatus controller 2. The user further prepares a therapy plan based on the image and inputs the therapy plan to the radiotherapy apparatus controller 2. The therapy plan indicates: irradiation angles, at each of which the therapeutic radiation is radiated to the affected part of the patient; and a dose and property of the therapeutic radiation radiated from each irradiation angle.

Figure 5:
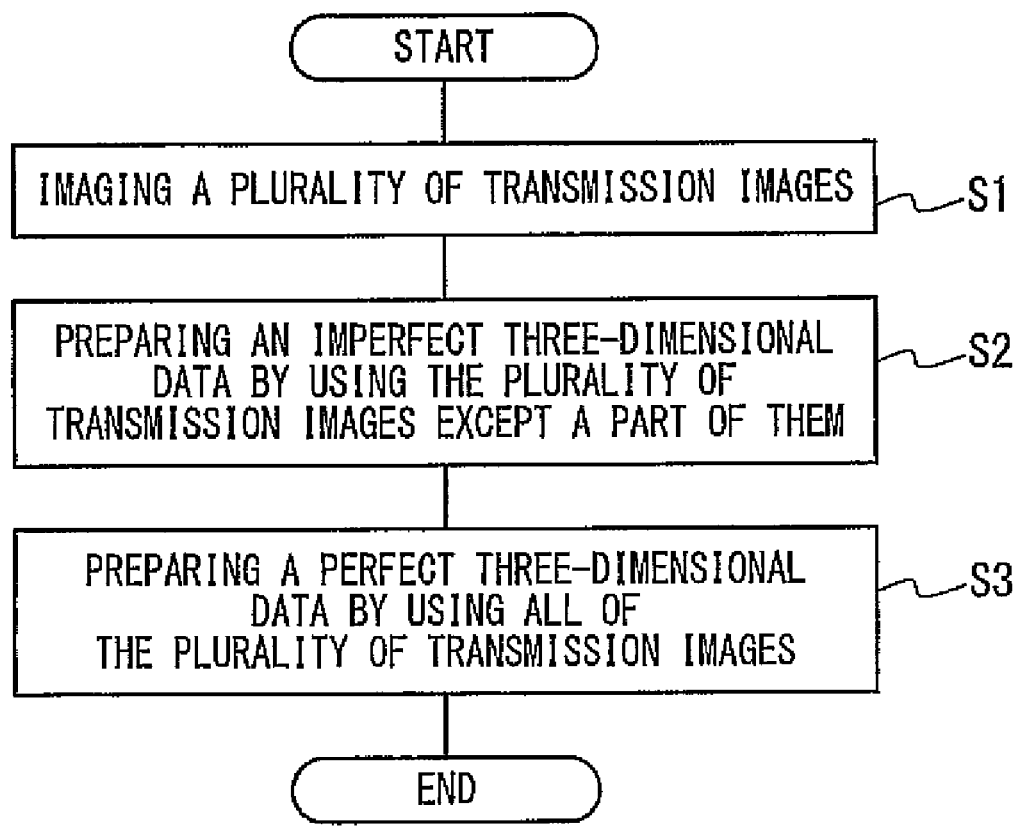
FIG. 5 is a flowchart showing an operation for preparing an imperfect three-dimensional data.

FIG. 5 shows the operation of preparing the imperfect three-dimensional data. The user firstly fixes the patient 43 onto the couch 41 in the radiotherapy apparatus 3, with the posture similar to that when the therapy plan was prepared. The radiotherapy apparatus controller 2 rotates the O-ring 12 around the rotational axis 17 and places the O-ring 12 at the O-ring rotation angle indicated in the therapy plan by using the pivoting driver 11. The radiotherapy apparatus controller 2 images the transmission image of the patient 43 by using the imager system in the radiotherapy apparatus 3, each time the traveling gantry 14 is rotated by 0.5 degrees around the rotational axis 18 by using the traveling driver in the radiotherapy apparatus 3 (Step S1). The radiotherapy apparatus controller 2 further correlates the plurality of transmission images to the angle information and temporarily records them in the storing unit.

The radiotherapy apparatus controller 2 calculates an imperfect three-dimensional data based on transmission images except a part of the transmission images in the plurality of imaged transmission images (Step S2). The part of the transmission images indicates a transmission image imaged by the imager system in the radiotherapy apparatus 3, when the therapeutic radiation irradiating apparatus 16 is arranged such that the therapeutic radiation 23 is radiated at each irradiation angle indicated by the therapy plan.

When there is a plurality of irradiation angles indicated by the therapy plan, the radiotherapy apparatus controller 2 calculates a plurality of imperfect three-dimensional data, for each of the plurality of irradiation angles. The imperfect three-dimensional data is calculated based on the plurality of transmission images except the transmission image imaged by the imager system in the radiotherapy apparatus 3 when the therapeutic radiation irradiating apparatus 16 is arranged such that the therapeutic radiation 23 is radiated from the corresponding irradiation angle.

The radiotherapy apparatus controller 2 repeats the operations of the steps S1, S2 a plurality of times. With such a repetition, the radiotherapy apparatus controller 2 can image the transmission images when the positions of the affected part of the patient 43 are different from each other, and can calculate the plurality of imperfect three-dimensional data indicating the affected parts that are placed at the plurality of positions different from each other.

The radiotherapy apparatus controller 2 calculates one reference perfect three-dimensional data by using all of the plurality of transmission images imaged at the step S1 (Step S3).

Figure 6:
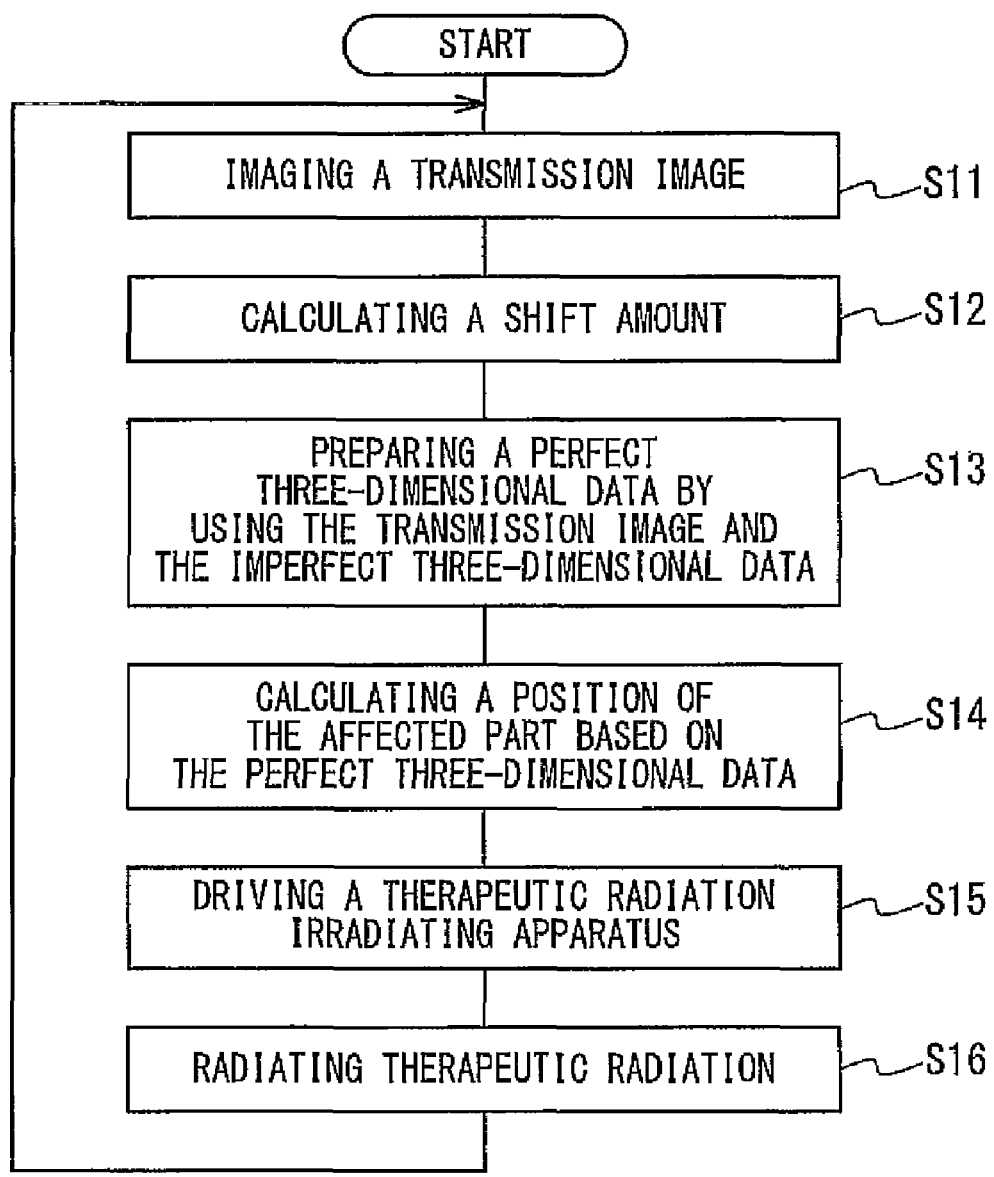
FIG. 6 is a flowchart showing an operation for carrying out radiotherapy.

FIG. 6 shows the operation of carrying out the radiotherapy. The radiotherapy apparatus controller 2 drives the therapeutic radiation irradiating apparatus 16 so that the therapeutic radiation 23 is irradiated at the irradiation angle indicated by the therapy plan which is prepared by the therapy planning unit 50, after the execution of the operation of preparing the imperfect three-dimensional data. That is, in the radiotherapy apparatus controller 2, the pivoting driver 11 is used to rotate the O-ring 12 around the rotational axis 17, and the O-ring 12 is consequently placed at the O-ring rotation angle indicated by the therapy plan, and the traveling driver in the radiotherapy apparatus 3 is used to rotate the traveling gantry 14 around the rotational axis 18, and the traveling gantry 14 is consequently placed at the gantry rotation angle indicated by the therapy plan.

The radiotherapy apparatus controller 2, after driving the therapeutic radiation irradiating apparatus 16, images the transmission image of the patient 43 by using the imager system in the radiotherapy apparatus 3 (Step S11).

The radiotherapy apparatus controller 2 calculates a shift amount based on the imperfect three-dimensional data calculated in the operation of preparing the imperfect three-dimensional data and the imaged transmission image (Step S12). That is, the radiotherapy apparatus controller 2 calculates a plurality of post-shift transmission images, in which an image shown in the transmission image is slightly shifted and shown. The radiotherapy apparatus controller 2 calculates a plurality of perfect three-dimensional data, based on each of the calculated post-shift transmission images and the imperfect three-dimensional data, for each of the plurality of calculated post-shift transmission images. The radiotherapy apparatus controller 2 selects the perfect three-dimensional data having the smallest difference from the reference perfect three-dimensional data that is calculated in the operation of preparing the imperfect three-dimensional data, from the plurality of calculated perfect three-dimensional data. The radiotherapy apparatus controller 2 calculates a shift amount based on the post-shift transmission image used to calculate the selected perfect three-dimensional data and the transmission image imaged at the step S11.

The radiotherapy apparatus controller 2 calculates a post-shift transmission image, in which an image shown in the transmission image imaged at the step S11 is shifted by the shift amount and shown. The radiotherapy apparatus controller 2 calculates a perfect three-dimensional data based on the post-shift transmission image and the imperfect three-dimensional data (Step S13). When there is the plurality of imperfect three-dimensional data, the radiotherapy apparatus controller 2 prepares a plurality of perfect three-dimensional data, based on the post-shift transmission image and each of the imperfect three-dimensional data, for each of the plurality of imperfect three-dimensional data, and calculates a perfect three-dimensional data having the smallest difference from the reference perfect three-dimensional data in the plurality of perfect three-dimensional data. The radiotherapy apparatus controller 2 calculates a sectional slice image of the patient 43, based on the calculated perfect three-dimensional data and displays the slice image on the display.

The radiotherapy apparatus controller 2 calculates a position of the affected part of the patient 43 based on the perfect three-dimensional data (Step S14). The radiotherapy apparatus controller 2 drives the therapeutic radiation irradiating apparatus 16 by using the head swinging mechanism 15 so that the therapeutic radiation 23 is transmitted through the calculated position, and controls a shape of the irradiation field of the therapeutic radiation 23 by using the MLC 20. The radiotherapy apparatus controller 2, after driving the head swinging mechanism 15 and the MLC 20, radiates the therapeutic radiation 23 by using the therapeutic radiation irradiating apparatus 16, in periods when the diagnosis X-rays 35, 36 are not radiated (Step S16).

The radiotherapy apparatus controller 2 cyclically repeats the operations of the steps S11 to S16, until the therapeutic radiation 23 of the dose indicated in the therapy plan are radiated to the affected part of the patient 43. As the cycle, 0.2 seconds are exemplified.

Typically, the perfect three-dimensional data can be faster calculated based on the additional transmission image and the imperfect three-dimensional data, as compared with the calculation based on the plurality of transmission images which are respectively imaged from the plurality of directions. Thus, according to such operations, the radiotherapy apparatus controller 2 can calculate the perfect three-dimensional data at the high speed, which enables the moving body tracking irradiation to be sufficiently performed on the position of the moving affected part, and can calculate the position of the affected part.

Typically, the position of the affected part that is calculated based on such three-dimensional data is higher in precision than the position of the affected part that is calculated based on the two transmission images. Thus, according to such operations, in the radiotherapy apparatus controller 2, the position can be calculated with the higher precision, as compared with the calculation of the position in which only the transmission image imaged at the step S11 is used without using the plurality of transmission images imaged in advance. As a result, the radiotherapy system 1 can irradiate the affected part of the patient 43 with the therapeutic radiation 23 with the higher precision and can reduce the dose of the therapeutic radiation radiated to the normal cell which differs from the affected part.

According to the configuration for selecting one perfect three-dimensional data from the plurality of perfect three-dimensional data that is respectively calculated from the plurality of imperfect three-dimensional data each having the different position of the affected part of the patient 43, the radiotherapy apparatus controller 2 can use the perfect three-dimensional data whose blur degree is small to calculate the position of the affected part and can calculate the position of the affected part with the higher precision.

Incidentally, the radiotherapy apparatus controller 2, when recording the plurality of imperfect three-dimensional data that is calculated for each of the plurality of irradiation angles indicated by the therapy plan, calculates the perfect three-dimensional data by using the calculated imperfect three-dimensional data except the transmission image imaged from the same direction as the transmission image imaged at the step S11. That is, such operations can be applied to a so-called Arc irradiotherapy, in which the therapeutic radiation irradiating apparatus 16 is moved during the execution of the operation of carrying out the radiotherapy.

Incidentally, the radiotherapy apparatus controller 2 can be designed at the step S16 so that, when the affected part is not placed at the predetermined position, the therapeutic radiation 23 is not radiated and when the affected part is placed at the predetermined position, the therapeutic radiation 23 is radiated. That is, the radiation irradiating method according to the present invention can be also applied to the radiotherapy in which the respiration synchronization irradiation (gated irradiation) is executed. At this time, the radiation irradiating method according to the present invention can detect the position of the affected part of the patient 43 with the higher precision and the higher speed and can irradiate the affected part of the patient 43 with the therapeutic radiation 23 with the higher precision, similarly to the above-mentioned embodiment.

Incidentally, the radiotherapy apparatus controller 2 can also execute the radiation irradiating method according to the present invention by using the radiotherapy apparatus that independently drives the therapeutic radiation irradiating apparatus and the imager system. Such radiotherapy apparatus is known and disclosed in, for example, Japanese Laid-Open Patent Application (JP-P 2006-21046A). At this time, the radiation irradiating method according to the present invention can detect the position of the affected part of the patient 43 with the higher precision and the higher speed and can irradiate the affected part of the patient 43 with the therapeutic radiation 23 with the higher precision, similarly to the above-mentioned embodiment.

The radiotherapy apparatus controller and the radiation irradiating method, according to the present invention, can detect the predetermined portion of the subject with the higher precision and the higher speed. As a result, the radiotherapy apparatus to which the radiotherapy apparatus controller or radiation irradiating method according to the present invention is applied can irradiate the predetermined portion of the subject with the therapeutic radiation with the higher precision.

The invention claimed is:

1. A radiotherapy apparatus controller comprising:
    an imperfect three-dimensional data calculating unit configured to calculate an imperfect three-dimensional data based on a plurality of imperfect transmission images which are respectively imaged from a plurality of imperfect directions except a predetermined direction among a plurality of directions different from each other;
    an imaging unit configured to image an additional transmission image from said predetermined direction by using an imager system;
    a perfect three-dimensional data calculating unit configured to calculate a perfect three-dimensional data based on said additional transmission image and said imperfect three-dimensional data;
    a position calculating unit configured to calculate a position of a part of a subject based on said perfect three-dimensional data; and
    a shift amount calculating unit configured to calculate a shift amount based on said additional transmission image and said imperfect three-dimensional data,
    wherein said perfect three-dimensional data calculating unit calculates said perfect three-dimensional data based on a post-shift transmission image in which an image shown in said additional transmission image is shifted by said shift amount and shown.

2. The radiotherapy apparatus controller according to claim 1, wherein
    said position calculating unit calculates said position of said part of said subject by comparing a reference perfect three-dimensional data, which is calculated based on a plurality of perfect transmission images respectively imaged from said plurality of directions, with said perfect three-dimensional data.

3. The radiotherapy apparatus controller according to claim 1, wherein said imperfect three-dimensional data includes:
    a first imperfect three-dimensional data, and
    a second imperfect three-dimensional data different from said first imperfect three-dimensional data,
    wherein said perfect three-dimensional data calculating unit prepares a first perfect three-dimensional data based on said additional transmission image and said first imperfect three-dimensional data, and calculates a second perfect three-dimensional data based on said additional transmission image and said second imperfect three-dimensional data, wherein said position calculating unit calculates said position based on one of said first imperfect three-dimensional data and said second imperfect three-dimensional data.

4. The radiotherapy apparatus controller according to claim 1, wherein
said imperfect three-dimensional data calculating unit calculates another imperfect three-dimensional data based on another plurality of imperfect transmission images which are respectively imaged from another plurality of imperfect directions except another predetermined direction different from said predetermined direction among said plurality of directions,
wherein said imaging unit images another additional transmission image from said another predetermined direction by using said imager system,
wherein said perfect three-dimensional data calculating unit calculates another perfect three-dimensional data based on said another additional transmission image and said another imperfect three-dimensional data, and
wherein said position calculating unit calculates a position of a part of said subject based on said another perfect three-dimensional data.

5. The radiotherapy apparatus controller according to any of claims 1, 2, 3, or 4, further comprising:
an irradiation controller configured to drive a therapeutic radiation irradiating apparatus radiating said therapeutic radiation based on said position.

6. The radiotherapy apparatus controller according to claim 5, wherein
said therapeutic radiation irradiating apparatus is supported to be moved integrally with said imager system.

7. A radiotherapy system comprising:
a radiotherapy apparatus controller;
a therapeutic radiation irradiating apparatus; and
an imager system,
wherein said radiotherapy apparatus controller includes:
an imperfect three-dimensional data calculating unit configured to calculate an imperfect three-dimensional data based on a plurality of imperfect transmission images which are respectively imaged from a plurality of imperfect directions except a predetermined direction among a plurality of directions different from each other;
an imaging unit configured to image an additional transmission image from said predetermined direction by using an imager system;
a perfect three-dimensional data calculating unit configured to calculate a perfect three-dimensional data based on said additional transmission image and said imperfect three-dimensional data;
a position calculating unit configured to calculate a position of a part of a subject based on said perfect three-dimensional data; and
a shift amount calculating unit configured to calculate a shift amount based on said additional transmission image and said imperfect three-dimensional data.,
wherein said perfect three-dimensional data calculating unit calculates said perfect three-dimensional data based on a post-shift transmission image in which an image shown in said additional transmission image is shifted by said shift amount and shown.

8. The radiotherapy system according to claim 7, wherein said position calculating unit calculates said position of said part of said subject by comparing a reference perfect three-dimensional data, which is calculated based on a plurality of perfect transmission images respectively imaged from said plurality of directions, with said perfect three-dimensional data.

9. The radiotherapy system according to claim 7, wherein said imperfect three-dimensional data includes:
a first imperfect three-dimensional data, and
a second imperfect three-dimensional data different from said first imperfect three-dimensional data,
wherein said perfect three-dimensional data calculating unit prepares a first perfect three-dimensional data based on said additional transmission image and said first imperfect three-dimensional data, and calculates a second perfect three-dimensional data based on said additional transmission image and said second imperfect three-dimensional data,
wherein said position calculating unit calculates said position based on one of said first imperfect three-dimensional data and said second imperfect three-dimensional data.

10. The radiotherapy system according to claim 7, wherein said imperfect three-dimensional data calculating unit calculates another imperfect three-dimensional data based on another plurality of imperfect transmission images which are respectively imaged from another plurality of imperfect directions except another predetermined direction different from said predetermined direction among said plurality of directions,
wherein said imaging unit images another additional transmission image from said another predetermined direction by using said imager system,
wherein said perfect three-dimensional data calculating unit calculates another perfect three-dimensional data based on said another additional transmission image and said another imperfect three-dimensional data, and
wherein said position calculating unit calculates a position of a part of said subject based on said another perfect three-dimensional data.

11. The radiotherapy system according to any of claims 7, 8, 9, or 10, wherein said radiotherapy apparatus controller further includes:
an irradiation controller configured to drive a therapeutic radiation irradiating apparatus radiating said therapeutic radiation based on said position.

12. The radiotherapy system according to claim 11, wherein
said therapeutic radiation irradiating apparatus is supported to be moved integrally with said imager system.

13. A radiation irradiating method comprising:
calculating an imperfect three-dimensional data based on a plurality of imperfect transmission images which are respectively imaged from a plurality of imperfect directions except a predetermined direction among a plurality of directions different from each other;
imaging an additional transmission image from said predetermined direction by using an imager system;
calculating a perfect three-dimensional data based on said additional transmission image and said imperfect three-dimensional data;
calculating a position of a part of a subject based on said perfect three-dimensional data and
calculating a shift amount based on said additional transmission image and said imperfect three-dimensional data,
wherein said perfect three-dimensional data is calculated based on a post-shift transmission image in which an image shown in said additional transmission image is shifted by said shift amount and shown.

14. The radiation irradiating method according to claim 13, wherein
said position is calculated by comparing a reference perfect three-dimensional data, which is calculated based on a plurality of perfect transmission images respectively imaged from said plurality of directions, with said perfect three-dimensional data.

15. The radiation irradiating method according to claim 13, wherein said imperfect three-dimensional data includes:
a first imperfect three-dimensional data, and
a second imperfect three-dimensional data different from said first imperfect three-dimensional data,
wherein said position is calculated based on one of a first perfect three-dimensional data prepared based on said additional transmission image and said first imperfect three-dimensional data and a second perfect three-dimensional data prepared based on said additional transmission image and said second imperfect three-dimensional data.

16. The radiation irradiating method according to claim 13, further comprising:
calculating another imperfect three-dimensional data based on another plurality of imperfect transmission images which are respectively imaged from another plurality of imperfect directions except another predetermined direction different from said predetermined direction among said plurality of directions;
imaging another additional transmission image from said another predetermined direction by using said imager system;
calculating another perfect three-dimensional data based on said another additional transmission image and said another imperfect three-dimensional data; and
calculating a position of a part of said subject based on said another perfect three-dimensional data.

17. The radiation irradiating method according to any of claims 13, 14, 15, or 16, further comprising:
driving a therapeutic radiation irradiating apparatus radiating said therapeutic radiation based on said position.

18. A computer program product for a radiation irradiating method, embodied on a non-transitory computer-readable medium and comprising code that, when executed, causes a computer to perform the following:
calculating an imperfect three-dimensional data based on a plurality of imperfect transmission images which are respectively imaged from a plurality of imperfect directions except a predetermined direction among a plurality of directions different from each other;
imaging an additional transmission image from said predetermined direction by using an imager system;
calculating a perfect three-dimensional data based on said additional transmission image and said imperfect three-dimensional data;
calculating a position of a part of a subject based on said perfect three-dimensional data; and
calculating a shift amount based on said additional transmission image and said imperfect three-dimensional data,
wherein said perfect three-dimensional data is calculated based on a post-shift transmission image in which an image shown in said additional transmission image is shifted by said shift amount and shown.

19. The computer program product according to claim 18, wherein
said position is calculated by comparing a reference perfect three-dimensional data, which is calculated based on a plurality of perfect transmission images respectively imaged from said plurality of directions, with said perfect three-dimensional data.

20. The computer program product according to claim 18, wherein said imperfect three-dimensional data includes:
a first imperfect three-dimensional data, and
a second imperfect three-dimensional data different from said first imperfect three-dimensional data,
wherein said position is calculated based on one of a first perfect three-dimensional data prepared based on said additional transmission image and said first imperfect three-dimensional data and a second perfect three-dimensional data prepared based on said additional transmission image and said second imperfect three-dimensional data.

21. The computer program product according to claim 18, further comprising:
calculating another imperfect three-dimensional data based on another plurality of imperfect transmission images which are respectively imaged from another plurality of imperfect directions except another predetermined direction different from said predetermined direction among said plurality of directions;
imaging another additional transmission image from said another predetermined direction by using said imager system;
calculating another perfect three-dimensional data based on said another additional transmission image and said another imperfect three-dimensional data; and
calculating a position of a part of said subject based on said another perfect three-dimensional data.

22. The computer program product according to any of claims 18, 19, 20, or 21, further comprising:
driving a therapeutic radiation irradiating apparatus radiating said therapeutic radiation based on said position.

* * * * *